(12) United States Patent  
Clark

(10) Patent No.: US 6,714,295 B2
(45) Date of Patent: Mar. 30, 2004

(54) OPTICAL INSPECTION METHOD AND APPARATUS HAVING AN ENHANCED HEIGHT SENSITIVITY REGION AND ROUGHNESS FILTERING

(75) Inventor: Bryan Kevin Clark, Mountain View, CA (US)

(73) Assignee: Beyond 3, Inc., Fremont, CA (US)

( * ) Notice: Subject to any disclaimer, the term of this patent is extended or adjusted under 35 U.S.C. 154(b) by 0 days.

(21) Appl. No.: 10/002,425

(22) Filed: Oct. 23, 2001

(65) Prior Publication Data

US 2003/0076490 A1 Apr. 24, 2003

(51) Int. Cl.[7] .............................................. G01N 21/00
(52) U.S. Cl. .................................................. 356/237.2
(58) Field of Search ........................ 356/237.1, 237.2, 356/237.3, 237.4, 237.5, 480, 370, 450, 519, 600, 512, 506; 359/738, 619, 321, 558; 250/306–309, 201.3, 216

(56) References Cited

U.S. PATENT DOCUMENTS

| | | | | |
|---|---|---|---|---|
| 3,901,597 A | * | 8/1975 | White | ...................... 356/4.05 |
| 4,334,780 A | * | 6/1982 | Pernick | ...................... 356/512 |
| 4,465,371 A | * | 8/1984 | Pernick | ................... 356/237.2 |
| 4,659,224 A | * | 4/1987 | Monchalin | ................... 356/502 |
| 5,220,403 A | * | 6/1993 | Batchelder et al. | ......... 356/450 |
| 6,522,471 B2 | * | 2/2003 | Clark | ........................ 359/629 |

* cited by examiner

Primary Examiner—Hoa Q. Pham
(74) Attorney, Agent, or Firm—Andrew M. Harris; Jeffrey D. Moy; Weiss, Moy & Harris, P.C.

(57) ABSTRACT

An optical inspection method and apparatus having an enhanced height sensitivity region and roughness filtering uses a Fabry-Perot cavity to increase the phase detection sensitivity for light reflected from surface defects having a height above a predetermined level. A partially reflective surface is inserted between an illumination subsystem and a surface under inspection. The position of the partially reflective surface with respect to the surface under inspection is adjusted to provide both filtering of defects below the predetermined level and enhance sensitivity for a region of defect heights above the predetermined level. The angular resolution of the inspection system is improved, providing far-field inspection that can detect small-profile defects having unacceptable heights. Media storage, semiconductor wafer and other precision surface manufacture may be improved by use of the techniques of the present invention.

23 Claims, 7 Drawing Sheets

Signal values for prior art phase contrast system

Signals for prior art phase contrast system

Signal values for enhanced phase contrast system

OPTICAL INSPECTION METHOD AND APPARATUS HAVING AN ENHANCED HEIGHT SENSITIVITY REGION AND ROUGHNESS FILTERING

RELATED APPLICATIONS

This application is related to pending U.S. patent application Ser. No. 09/789,913 entitled "SYSTEM OF BEAM NARROWING FOR RESOLUTION ENHANCEMENT AND METHOD THEREFOR" filed on Feb. 21, 2001, the specification of which is incorporated in herein by reference.

BACKGROUND OF THE INVENTION

1. Field of the Invention

This invention relates to optical inspection systems, and more specifically, to an optical system incorporating a resonator to produce an enhanced sensitivity to defects with significant height and a filtering of surface roughness.

2. Description of the Related Art

Precision surfaces are required in components used in many applications today. Storage media for use in both for optical and magnetic storage systems require surfaces that are free of defects having significant height above the mean surface of the media. If a defect sufficiently high collides with the storage system head assembly, the storage system may be destroyed or damaged.

In semiconductor manufacturing, semiconductor material is etched from and deposited on a silicon wafer. Yield of semiconductors is dependent on defect-free regions on the surface of the wafers. Defects of significant height may cause shorting between layers within an integrated circuit and may also reduce reliability of integrated circuits that appear otherwise functional after manufacture.

In the manufacturing process, it is necessary to inspect media, wafers and other surfaces to determine whether or not they are manufactured to the tolerances demanded by functional requirements and to make necessary adjustments in the manufacturing process to avoid manufacturing defective components.

Near field inspection systems may be used to resolve small defects, but since the near-field is confined to a relatively small height above the surface under inspection, it must scan the surface very slowly to avoid collision with the surface and if defects of significant height exist, the near-field probe may be damaged by collision with a defect.

Present far-field inspection systems use interferometric techniques to determine surface height by reflecting and measuring an optical beam off the surface under inspection. However, standard far-field inspection systems are unsuitable for detecting small profile defects having significant height to above the average surface.

Any optical inspection system has resolution limits. Within a resolution cell dictated by the resolution limits, the reflected field will be averaged from all points within the aperture of the resolution cell. The resolution cell limits are both angular and linear and are affected by surface characteristics in that very small surface features disperse a reflected field over a wide angle. Small sub-wavelength defects and surface variations approach point source behavior, which will cause reflected energy to be dispersed throughout a half-plane (180 degree solid angle) above a surface under inspection.

Within the resolution cell of an optical inspection system, the received reflected energy is averaged. A defect that is significantly smaller than the resolution cell and having a height or depth that is slightly greater than the acceptable surface roughness will produce an optical signal that is indistinguishable in the presence of the "speckle noise" produced by the surface roughness.

Due to the angular spectrum of small defect reflections (reflecting into approximately the entire half-plane) and the resulting interference with surface roughness variations within the resolution cell being measured, the sensitivity of existing far-field inspection systems to small (sub-wavelength) defects is further reduced.

In essence, a wide-profile deviation of nominal depth or height that is acceptable, may produce the same or greater inspection signature as a very small-profile defect of unacceptable height. Therefore existing far-field optical systems cannot discriminate between small defects and normal roughness variations. Thus, existing far-field optical inspection systems are unsuitable for inspecting surfaces for small defects. Since the profile of a defect that may cause damage to a media storage device or shorting in an integrated circuit wafer may be very small, existing far-field inspection systems are unsuitable for detecting the above-mentioned defects.

Therefore, it would be desirable to provide a far-field inspection method and apparatus having an enhanced sensitivity to defect height. It would further be desirable to provide an inspection method and apparatus having a filtering characteristic for reducing the impact of surface roughness on inspection sensitivity. It would further be desirable to provide a far-field inspection method and apparatus that reduce the angular spectrum of reflections from a small defect to improve discrimination between small defects and surface roughness.

SUMMARY OF THE INVENTION

The foregoing objectives are achieved in an optical inspection method and apparatus having an enhanced height sensitivity region and roughness filtering. The inspection apparatus includes an optical illumination system for producing a beam for illuminating a surface under inspection, a detector for detecting intensity of light reflected from the surface under inspection, and a partially reflective surface positioned between the illumination subsystem and the surface for forming an optical resonator between the partially reflective surface and the surface under inspection. The resonator improves the sensitivity of the detector to reflections from defects having a height exceeding a predetermined height. The sensitivity is increased due to multiple reflections within the resonator. The resonator may be tuned so that the sensitivity of the inspection system is decreased for surface variations below a predetermined value and increased for variations above the predetermined value, so that filtering of acceptable roughness variation is achieved. The resonator also reduces the angular spectrum of reflections from small defects.

The foregoing and other objects, features, and advantages of the invention will be apparent from the following, more particular, description of the preferred embodiment of the invention, as illustrated in the accompanying drawings.

DESCRIPTION OF EMBODIMENTS OF THE INVENTION

Figure 1:
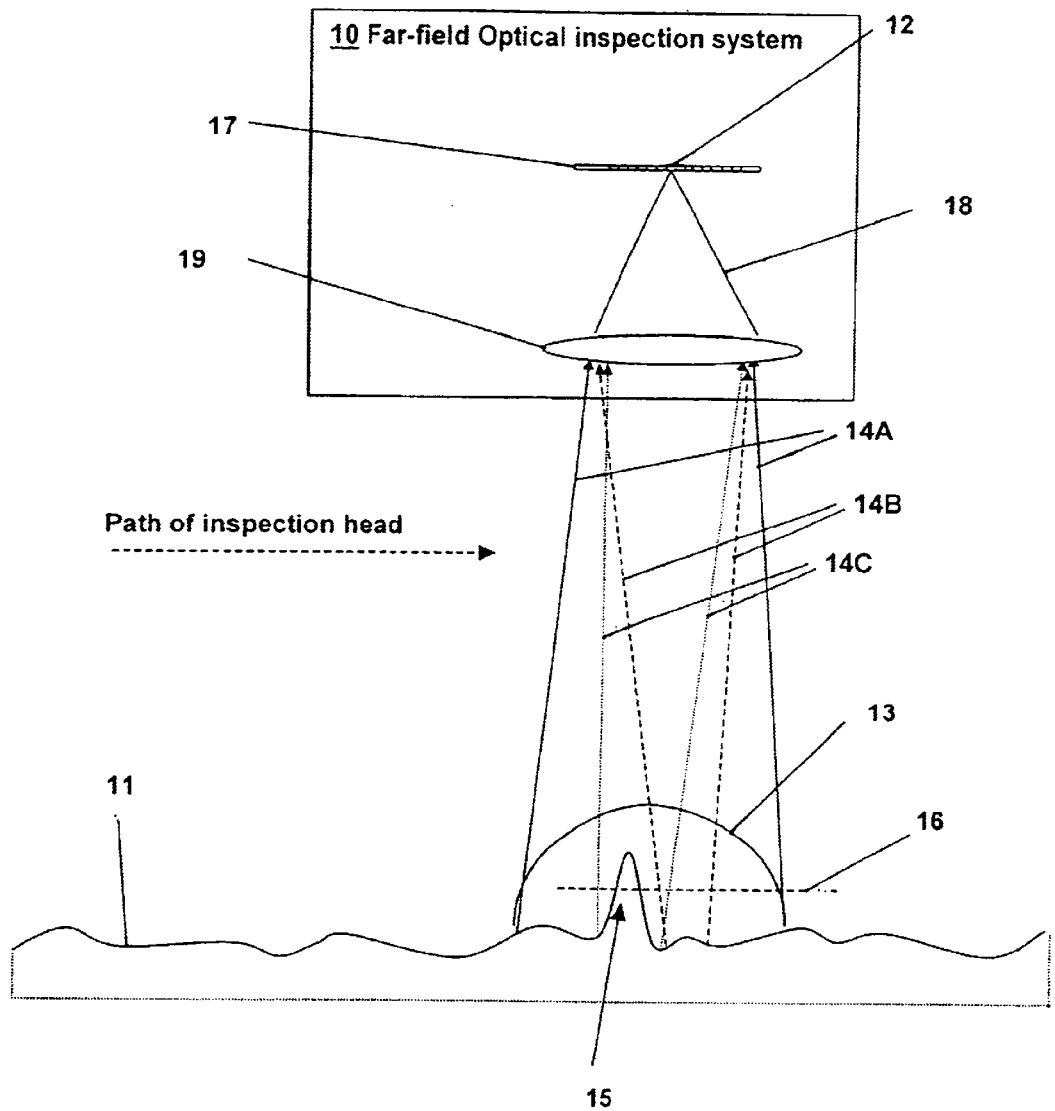
FIG. 1 is an illustration depicting a cross section of a surface under inspection by a prior art inspection system.

With reference now to the figures, and particularly to FIG. 1, a surface 11 under inspection by a prior art far-field optical inspection system 10 is depicted. Optical inspection system 10 is commonly known as an interferometric contrast microscope. Optical inspection system 10 includes a detector 12 shown here as a charge-coupled device (CCD) linear array, but other suitable detectors may be used. A lens 19 images light reflected from a resolution cell 13 on surface 11 to a cell of CCD 12. The illumination path is not depicted in the illustration, nor is a reference path, as it is the reflected light that is pertinent to the description of the differences between the prior art and the present invention. Several resolution cells may thereby be scanned by detector 12 without moving the inspection head. Resolution cell 13 represents the optical resolution of imaging lens 19.

An illumination beam (not shown) is reflected by surface 11 to produce a reflected beam 14A. The reflected beam is comprised of wavefronts from surface 11 including reflections from surface variations 14B and reflections 14C from a defect 15. The resolution aperture 13 encompasses all of the above reflections, vector summing each of the reflections. Resolution aperture 13 in practice is much larger than defect 15, but the size of defect 15 has been increased in the figure for illustrative purposes.

In the vicinity of surface features (roughness, defects, etc.), speckle noise is produced, creating a field that extends over aperture 13. While it would be desirable to use a far-field system such as optical inspection system 10 for high-speed scanning of such surfaces as storage device platters, it is not practical due to the inability of optical inspection system 10 to distinguish small-profile defects such as defect 15 that are of a height greater than an acceptable threshold 16.

Since optical inspection system 10 via detector cell 12 averages all of the reflections received from resolution cell 13, and since defect 15 is significantly smaller than resolution cell 13, defect 15 will produce an optical signal that is indistinguishable in the presence of the speckle noise produced by the surface roughness.

For example, assume optical inspection system 10 has a resolution of 2 $\mu$m and inspects a surface having a roughness variation of 0.002 $\mu$m peak-to-valley with an acceptance/defect limit of 0.01 $\mu$m height. If defect 15 has a diameter of 0.2 $\mu$m in the plane normal to surface 11, the area of defect 15 is approximately 1% of the resolution cell area. Although the height of defect 15 is greater than the roughness variation by a factor of 5, the speckle noise will be greater than the optical signal from defect 15 by a factor of 20, as the roughness signal (producing speckle noise) extends over the resolution cell which has an area greater by a factor of 100.

Therefore, standard far-field inspection systems such as prior art far-field optical inspection system 10 are unable to detect defects that will render a surface unacceptable or needing modification via machining, laser modification or other technique.

Figure 2A:
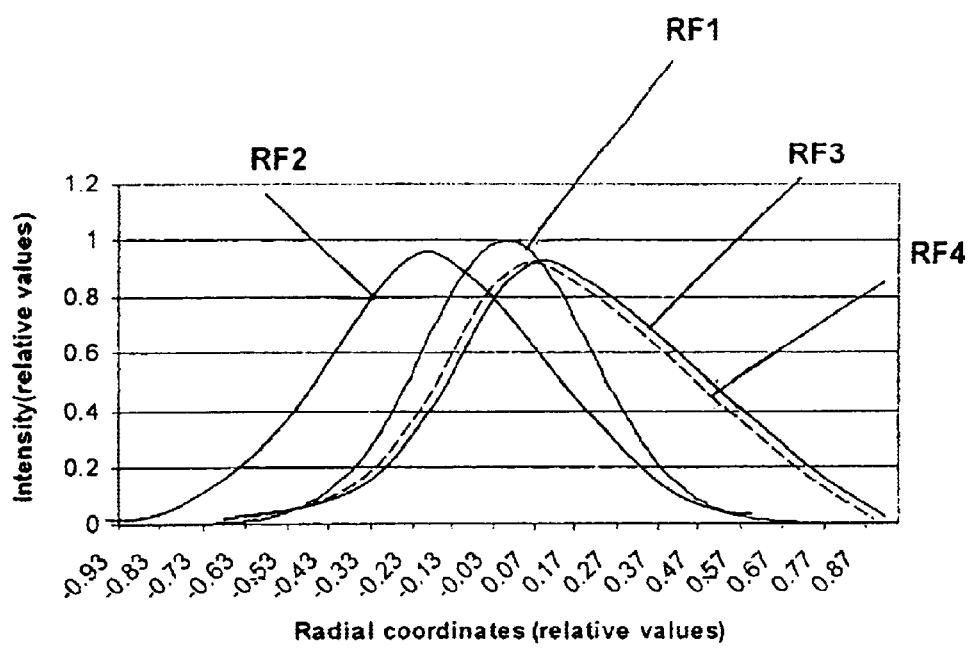
FIG. 2A is a graph depicting optical images generated by prior art inspection system 10 of FIG. 1.

Referring now to FIG. 2A the above-described problem with prior art far-field measurement systems is depicted in graphical form. The graph shows relative intensity of the response of the received optical signal as a function of the surface displacement relative to the optical inspection head. Curve RF1 shows the response from an ideally flat reflective surface. Curve RF2 shows the maximum expected deviation of the image signal due to surface roughness for one position of the inspection head (or roughness location), while curve RF3 shows the maximum expected deviation of the image signal in the other direction, for a different position of the inspection head. The actual signal variations due to acceptable surface roughness are expected to fall between curves RF2 and RF3. A significant deviation from this range indicates the presence of a defect. Curve RF4 shows the same image as curve RF3 for a surface having a small defect within the resolution aperture. As can be seen from the graph, the deviation of the image signal in the presence of a defect is slight with respect to the deviations due to normal surface roughness. For the case illustrated, the deviation signal variation lies within the range of acceptable roughness signal variation and therefore, the defect is not detectable using an inspection system having the above-described characteristics.

Figure 2B:
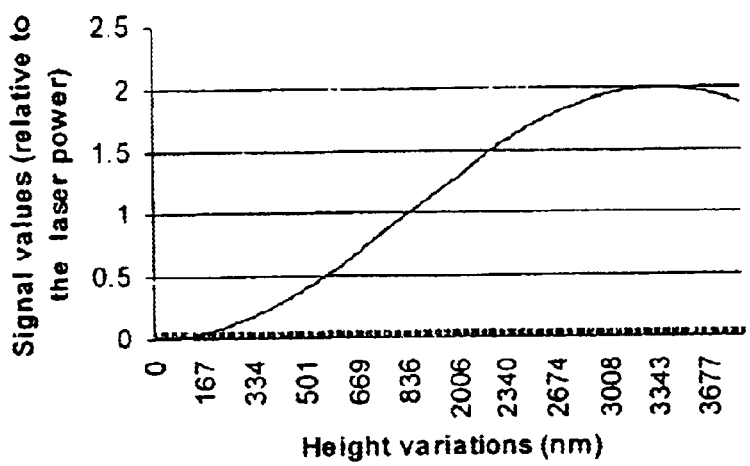
FIG. 2B and FIG. 2C are graphs depicting the sensitivity of the prior art system of FIG. 1.

Referring now to FIG. 2B, the underlying low sensitivity of prior art far-field measurement systems to small height variations is depicted in graphical form. As seen in the graph, variation in detected signal power continuously increases for height variations from zero to over 3000 nanometers, from which the power returned is twice the laser power (for a totally reflective surface). However, the surfaces of interest in storage media and other applications may fall in the range of the graph below 20 nanometers, where the energy returned is miniscule.

Figure 2C:
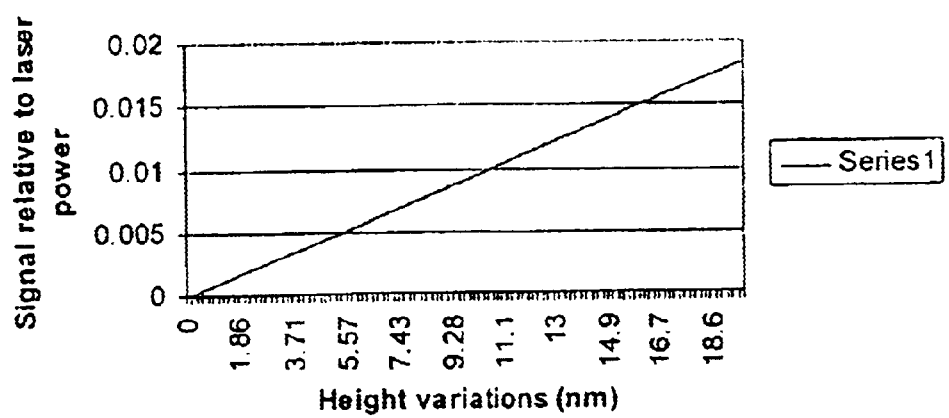

Referring to FIG. 2C, the region of interest from FIG. 2B is expanded and is depicted for a system wherein the interferometric contrast is optimized for height variations below 0.02 $\mu$m (otherwise the slope of the signal curve would be even lower, resulting in a lower sensitivity to small height variations). As can be seen from the graph, the signal around the average surface profile is practically linear and is still very small with respect to the total laser power, approaching a 2% return for height variations approaching 0.02 $\mu$m (20 nanometers).

The above-illustrated example can be analyzed using the graph of FIG. 2C. A defect 0.01 $\mu$m high with an area of 1% of the resolution aperture with a surface roughness of 0.002 $\mu$m peak-to-valley yields a peak-to-peak roughness signal (noise) of 0.25% and a defect signal component of 0.01%, yielding a peak signal-to-noise ratio of —13 dB, (1:20) indicating that the signal from the defect is undetectable in the presence of surface roughness.

Figure 3:
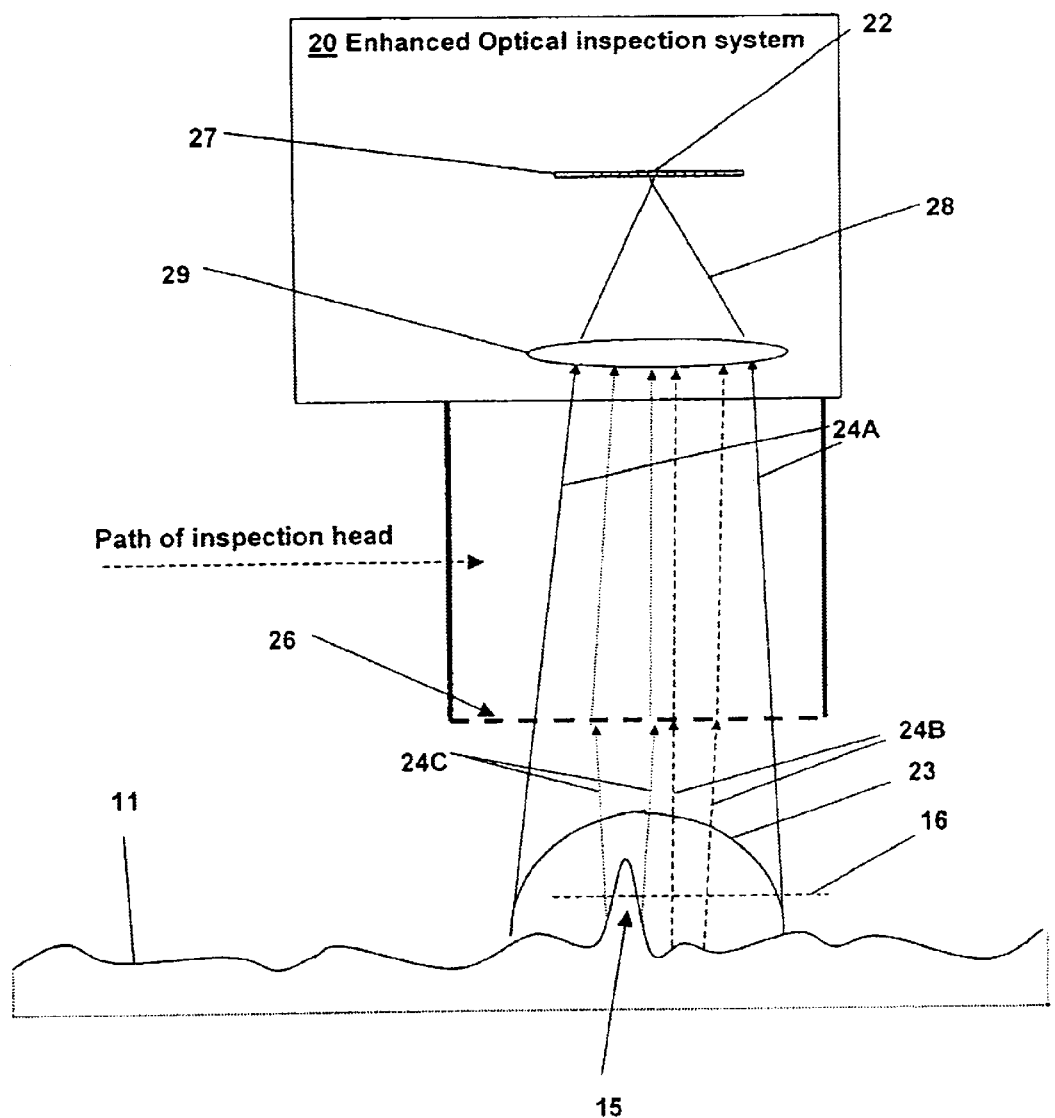
FIG. 3 is an illustration depicting a cross section of a surface under inspection by an apparatus in accordance with a preferred embodiment of the invention.

Referring now to FIG. 3, surface 11, under inspection by an enhanced optical inspection system 20 in accordance with a preferred embodiment of the present invention is depicted. A partially reflective surface 26 is incorporated within optical inspection system 20 producing an optical resonant cavity between partially reflective surface 26 and surface 11 under inspection. The resonance of the cavity is inherently highly non-linear and therefore it is possible to adjust the length of the cavity by varying the position of the partially reflective surface 26 to enhance a filtering effect. The filtering effect filters a reflected field from the surface, based strictly on the height of the surface.

Enhanced optical inspection system 20 includes a detector 27, which is depicted as a CCD array, although other suitable optical detectors may be used. A lens gathers reflected wavefronts 24A–24C from surface 11 and images the resolution cell 23 on surface 11 on CCD pixel 22 which averages the light reflected from resolution aperture 23. Reflected wavefront 24A represents the entire range of reflections from resolution aperture 23, while reflected wavefront 24B depicts a reflection from a roughness area and wavefront 24C depicts a reflection from defect 15. Note that in contrast to the illustration in FIG. 1, reflection 24C from defect 15 does not overlap reflection 24B from the roughness area and can therefore be more easily resolved by detector 27. The multiple reflections set up in the resonant cavity formed by partially reflective surface 26 and surface 11 are highly sensitive to angle, and therefore serve to separate reflections from surface features displaced from each other. Due to the small angular spectrum accepted by the resonant cavity, surface feature reflections will sum in image pixel 22 in a non-coherent manner, causing any interferences to be uncorrelated, significantly decreasing optical noise from surface 11.

The resonance of the cavity is inherently highly non-linear and therefore it is possible to adjust the length of the cavity to provide filtering of reflections based on surface height. The position of partially reflective surface 7 can be adjusted so that a resonance condition tuned to produce a higher overall reflected energy return for height variations within a region of interest (for example, 5 to 20 nanometers) and having a non-linear response with respect to height variation. The non-linear response produces a filtering effect. The filtering effect can be tuned to produce little signal variation for height variations below, for example, 5 nanometers, providing a rejection of most of the surface roughness variation, while returning a strong signal from defects having a height greater than 5 nanometers.

Due to the filtering effect and reduction in the field coupling between surface features, defect 15 can be detected as having a height exceeding acceptance threshold 16, by the techniques of the present invention. Thus, enhanced optical inspection system 20 can achieve results similar to a near-field inspection system, without placing a probe within the near-field region, by filtering out all of acceptable height variations.

Figure 4A:
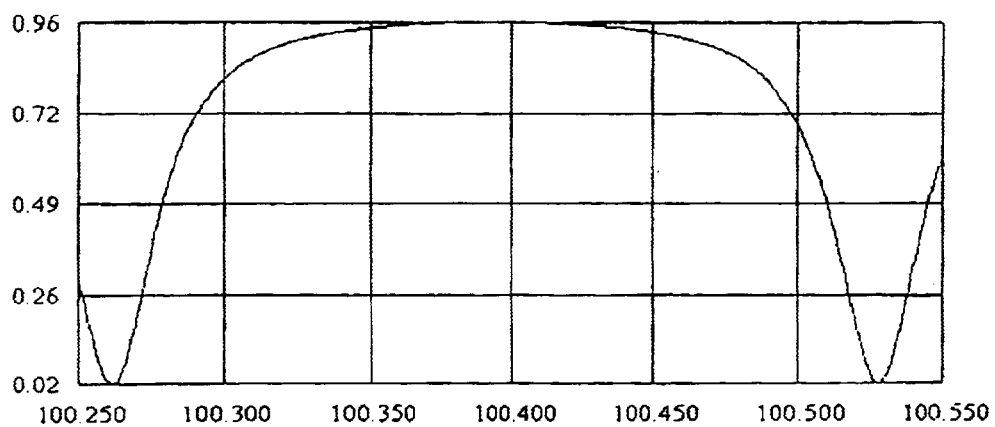
FIG. 4A and FIG. 4B are graphs depicting the enhanced sensitivity of the system of FIG. 3.

Referring now to FIG. 4A, the operation of the present invention is depicted in graphical form. For very low height variations, little or no laser power signal is detected, but above a threshold, the laser power returned increases rapidly to very high values. Thus, the detector sensitivity may be improved for inspecting surfaces having a region of interest for height variations, and the non-linear response for small height variations may be used to filter out acceptable surface roughness.

Figure 4B:
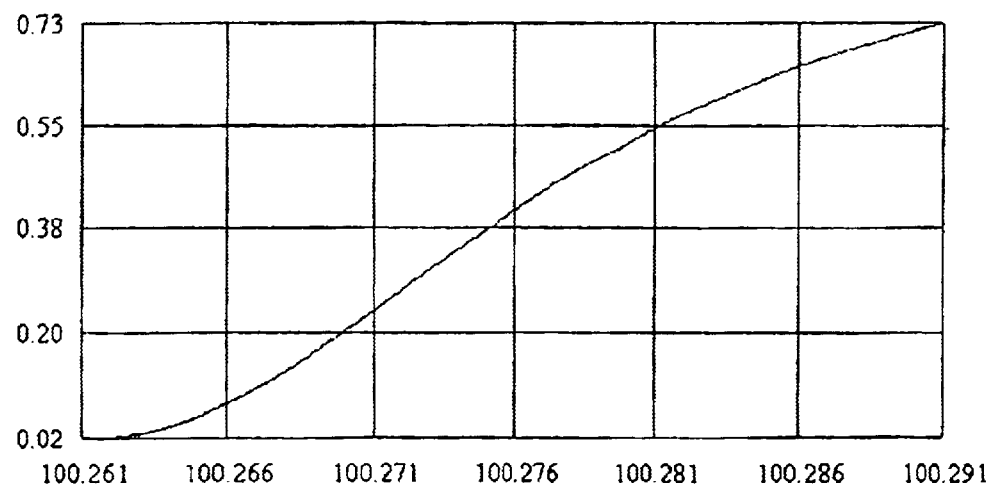

Referring now to FIG. 4B, the operation of the present invention over the exemplary region of interest is depicted. For height variations below 2 nanometers (from 100.261 $\mu$m to 100.263 $\mu$m on the graph), the signal variation with surface height is small, but above 2 nanometers (from 100.263 $\mu$m to 100.283 $\mu$m), the slope becomes linear and increases rapidly. Due the non-linear response of the resonant cavity to small height variations, the system will filter height variations bellow a given threshold and enhance all others. Note also the large signal comparative to the regular phase contrast—FIGS. 2A and 2B. The nonlinearity range of the resonant cavity depends on the reflectivity of the two surfaces forming the cavity and on the absorption of the tested surface.

From the graph depicted in FIG. 4B, a feature having a height of 20 nanometers will return approximately 55 percent of the laser power, while surface roughness below 2 nanometers will integrate to a much lower value than in the prior art system. Additionally, the reduction in field coupling to other surface features reduces the range of the surface features contributing to the roughness variation so that a 10 nanometer high defect will "stand out" in the detected signal.

Figure 5:
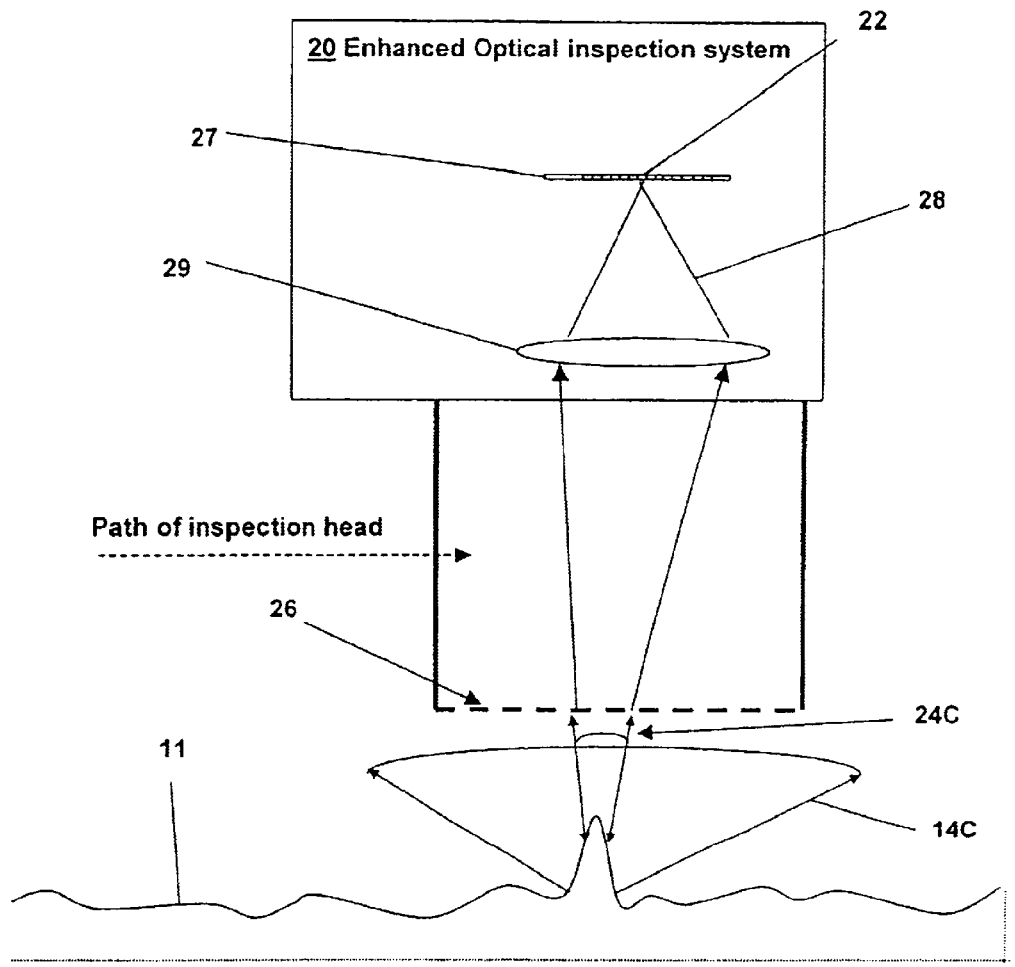
FIG. 5 is an illustration depicting a cross section of a surface under inspection showing an improvement in angular selectivity generated by an apparatus in accordance with a preferred embodiment of the invention.

The resonance condition between surface 11 and partially reflective surface 26 also reduces the angular spread of reflected beams 24A–24C, producing a system response that is much narrower than the reflected beams 14A–14C of FIG. 1 and system sensitivity to the interaction between closely spaced features creating speckle noise is greatly reduced. Referring now to FIG. 5, the improvement in angular rejection is illustrated. Between partially reflective surface 26 and surface of interest 11, the angles for which the resonance condition are supported are those angles very close to the axis normal to both surfaces, as both surfaces must be kept parallel. Thus, the angular spread of reflection 24C from defect 15 that is enhanced by the resonance condition is much smaller that the angular spread of reflection 14C from defect 15 in prior art optical inspection system 10. While in the prior art system, energy reflected from defect 15 will be spread through a wide angle, the resonance condition present in embodiments of the present invention ensures that most of the energy will be concentrated at angles very close to the normal axis between surface 11 and partially reflective surface 26.

Figure 6:
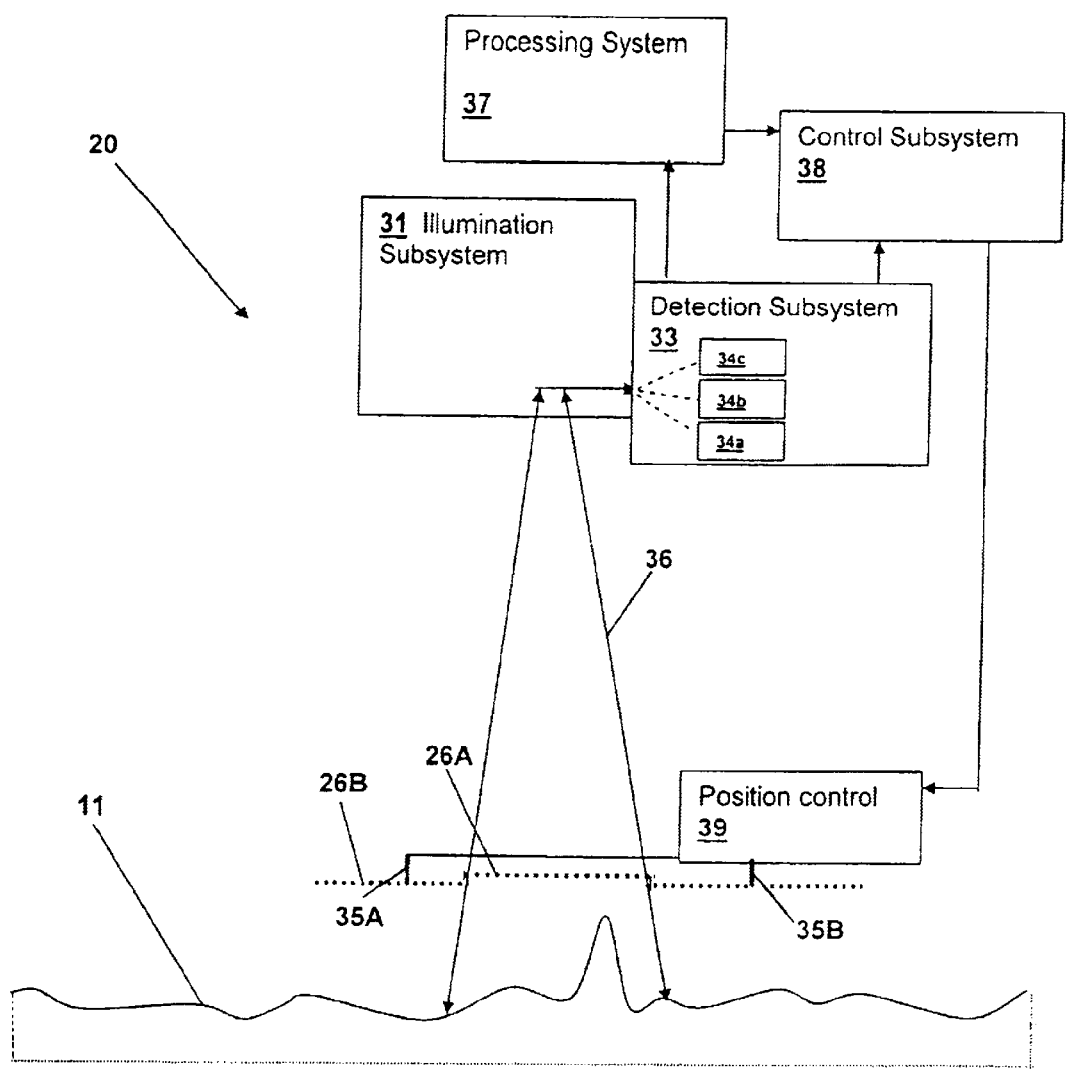
FIG. 6 is a block diagram depicting details of the apparatus of FIG. 3 inspecting a surface.

Referring now to FIG. 6, details of enhanced optical inspection system 20 are depicted. Illumination subsystem 31 produces a beam 36 that is directed at surface under inspection 11 through partially reflective surface 26A. Partially reflective surface 26A produces a Fabry-Perot optical resonant cavity with surface under inspection 11. At the distance at which partially reflective surface 26A and surface under inspection 11 form the optimal Fabry-Perot cavity, the sensitivity is greatest, due to the resonance condition of the Fabry-Perot cavity. Detection subsystem 33 provides detection of the reflected beam, permitting measurement of surface height variations. The presence of partially reflective surface 26A increases the sensitivity of the interferometer around the resonant distance of the Fabry-Perot cavity formed between the partially reflective surface 26A and surface under inspection 11.

A second tier 26B to partially reflective surface 26A, may be incorporated to provide a second resonant cavity having a second resonant length disposed around the central resonant cavity. This second resonant cavity is used for position control, permitting operation of detectors for determining surface tilt and average height at a separate operating point within the curves of FIGS. 4A and 4B. For example, a resonant distance set by second tier 26B that is 8 nanometers longer than resonant length set by partially reflective surface 26A, will result in a signal strength of 25% of the incident light and a sensitivity (slope) that is at a maximum for the graphs in the figures. This permits a pair of detectors, a quad photodiode array or a CCD detector to detect a second strong signal angularly disposed outside the circumference of the height detection central area for adjusting the position of partially reflective surface 26A (and consequently second tier 26B). If a CCD linear array detector is used, the intersections of the resonant band (annular) due to second tier 26B will be detectable at a pair of cells surrounding the cells receiving signal from the central area, thus the same detectors that are used for detecting the height-measuring interferometric signal at other positions within the scan may be used at other times for detecting surface tilt and average position.

Partially reflective surface 26A (and optionally second tier 26B) may be a lens within illumination subsystem 31 that may be positioned by positioners 35A and 35B and position control 38, a separate partially reflective plate again positioned by a positioners 35, or a coating or plate placed directly on surface under inspection 11.

A control subsystem 38 and position control 39 are used to move positioners 35A and 35B that are mechanically coupled to partially reflective surface 26A. Positioners 35A and 35B move partially reflective surface 26A (and consequently second tier 26B) to positions that track surface variations in order to maintain the resonance condition between partially reflective surface 26A and surface under inspection 11, so that the filtering effect and contrast enhancement are provided at the desired height above the average surface height. Positioners 35A and 35B likewise maintain the second resonance condition between the surface and second tier 26B (if incorporated) to maintain maximum position detection sensitivity.

A processing system 37 is coupled to detection subsystem 33 and position control 39, for controlling the position of partially reflective surface 26A in conformity with information received from detection subsystem 33. Processing system 37 may thereby adjust the position of partially reflective surface 26A to maximize the detection sensitivity for inspection of a region having a tilt or surface variation, which maintains the filtering effect and sensitivity in the region of interest. Detection subsystem may use multiple detectors 34a–34c aligned in different planes to detect surface tilt and height, such as the quad photodiode array mentioned above, or detection system may incorporate a linear CCD array and use peripheral cells to determine position and tilt. Position control 39 as configured moves positioners 35A and 35B independently to tilt and move partially reflective surface 26A to maintain a substantially parallel arrangement between partially reflective surface 21 and the region of surface under inspection 11 that is within the aperture of the optical inspection system.

While the invention has been particularly shown and described with reference to the preferred embodiments thereof, it will be understood by those skilled in the art that the foregoing and other changes in form, and details may be made therein without departing from the spirit and scope of the invention.

What is claimed is:

1. An optical inspection system for inspecting a surface under inspection, said inspection system comprising:
    an optical illumination system for producing a beam for illuminating a surface under inspection;
    a detector for measuring an intensity of light reflected from said surface under inspection;
    a partially reflective surface positioned at a tuned optical distance between said surface under inspection and said optical illumination system forming a resonator with said surface under inspection, whereby a signal generated by light reflected from defects on said surface under inspection that exceed a predetermined height is increased due to multiple reflections within said resonator; and
    a scanning system for moving said beam across said surface under inspection.

2. The optical inspection system of claim 1, wherein said resonator has a non-linear response with a height of said defects, whereby a signal generated by light reflected from artifacts that do not exceed said predetermined height is decreased.

3. The optical inspection system of claim 1, wherein said resonator comprises a partially reflective surface positioned substantially parallel to said surface under inspection between said optical illumination system and said surface under inspection and at a tuned optical distance from said surface under inspection, whereby a signal generated by light reflected from said defects exceeding said predetermined height is increased due to multiple reflections between said partially reflective surface and said surface under inspection.

4. The optical inspection system of claim 1, wherein said partially reflective surface is a coating deposited on said surface under inspection.

5. The optical inspection system of claim 1, wherein said partially reflective surface is a surface of an optical element contained within said optical illumination system.

6. The optical inspection system of claim 5, wherein said partially reflective surface is a coating deposited on said optical element.

7. The optical inspection system of claim 1, further comprising a positioner mechanically coupled to said partially reflective surface for positioning said partially reflective surface at a tuned optical distance from a region of said surface under inspection.

8. The optical inspection system of claim 7, further comprising a controller coupled to said positioner for adjusting said position of said partially reflective surface in response to a signal received from said detector.

9. The optical inspection system of claim 7, further comprising:
    a controller coupled to said positioner for adjusting said position of said partially reflective surface; and
    a processing system coupled to said controller.

10. The optical inspection system of claim 9, wherein said processing system is further coupled to an output of said detector, whereby said position is adjusted in conformity with said output of said detector.

11. The optical inspection system of claim 10, wherein said detector comprises a plurality of detectors for detecting a tilt of said surface under inspection, and wherein said processing system adjusts said position of said partially reflective surface to maintain said position of said partially reflective surface substantially parallel to a region of said surface under inspection.

12. The optical inspection system of claim 10, wherein said partially reflective surface includes a secondary tier positioned at a second tuned optical distance from said surface, and wherein said detector detects light that is transmitted through said secondary tier whereby sensitivity of said detector is improved.

13. An optical inspection system for inspecting a surface under inspection, said inspection system comprising:
    an optical illumination system for producing a beam for illuminating a surface under inspection;
    a detector for measuring an optical signal from light reflected from said surface under inspection;
    means for increasing an optical signal generated by light reflected from defects on said surface under inspection that exceed a predetermined height; and
    a scanning system for moving said beam across said surface under inspection.

14. The optical inspection system of claim 13, wherein said increasing means further comprises means for decreasing an optical signal generated by light reflected from defects that do not exceed said predetermined height.

15. The optical inspection system of claim 13, further comprising second increasing means for increasing an optical signal for controlling position of said first increasing means.

16. An optical inspection system for inspecting a surface under inspection, said inspection system comprising:
   an optical illumination system for producing a beam for illuminating a surface under inspection;
   a detector for measuring an optical signal from light reflected from said surface under inspection;
   means for decreasing an optical signal generated by light reflected from defects on said surface under inspection that do not exceed a predetermined height; and
   a scanning system for moving said beam across said surface under inspection.

17. A method for inspecting a surface under inspection, said method comprising:
   illuminating a partially reflective surface with an illumination beam from an illumination subsystem;
   illuminating said surface under inspection with a transmitted beam that is transmitted from said illumination beam through said partially reflective surface, wherein said partially reflective surface and said surface under inspection are positioned substantially parallel to each other and at a tuned optical distance such that a reflected beam reflected from defects on said surface under inspection that exceed a predetermined height has an increased signal sensitivity;
   positioning said beam at a location on said surface under inspection; and
   detecting said reflected beam from said defects.

18. The method of claim 17, further comprising depositing a coating on said surface under inspection including said partially reflective surface.

19. The method of claim 17, further comprising adjusting a position of said partially reflective surface.

20. The method of claim 19, wherein said adjusting is performed in response to said detecting.

21. The method of claim 20, wherein said adjusting adjusts a tilt of said partially reflecting surface in response to said detecting having detected that a region of said surface under inspection is tilted, such that said partially reflective surface and said region are maintained in a substantially parallel arrangement.

22. The method of claim 20, wherein said detecting detects a height of a region of said surface under inspection, and wherein said adjusting adjusts a height of said partially reflective surface such that said tuned optical distance is maintained between said region and said partially reflective surface.

23. The method of claim 17, wherein said partially reflective surface includes a second tier, and wherein said detecting further comprises second detecting light reflected through said second tier and wherein said adjusting is performed in response to said second detecting.

* * * * *